United States Patent
Heissenstein et al.

(10) Patent No.: US 9,905,014 B2
(45) Date of Patent: Feb. 27, 2018

(54) METHOD AND SYSTEM FOR THE EXAMINATION OF A SAMPLE BY MEANS OF THERMOGRAPHY

(71) Applicant: FEI EFA, Inc., Fremont, CA (US)

(72) Inventors: Hans Heissenstein, Wiesenttal (DE); Peter Stolz, Fürth (DE); Raiko Meinhardt-Wildegger, Erlangen (DE)

(73) Assignee: FEI EFA, Inc., Fremont, CA (US)

( * ) Notice: Subject to any disclaimer, the term of this patent is extended or adjusted under 35 U.S.C. 154(b) by 141 days.

(21) Appl. No.: 14/653,226

(22) PCT Filed: Nov. 13, 2013

(86) PCT No.: PCT/EP2013/073757
§ 371 (c)(1),
(2) Date: Jun. 17, 2015

(87) PCT Pub. No.: WO2014/095170
PCT Pub. Date: Jun. 26, 2014

(65) Prior Publication Data
US 2015/0339830 A1    Nov. 26, 2015

(30) Foreign Application Priority Data

Dec. 17, 2012    (EP) .................................... 12197611

(51) Int. Cl.
*G01J 5/02*    (2006.01)
*G01N 25/72*    (2006.01)
(Continued)

(52) U.S. Cl.
CPC ................ *G06T 7/20* (2013.01); *G01J 5/02* (2013.01); *G01N 25/72* (2013.01); *G06K 9/52* (2013.01);
(Continued)

(58) Field of Classification Search
None
See application file for complete search history.

(56) References Cited

U.S. PATENT DOCUMENTS

| | | | | |
|---|---|---|---|---|
| 6,394,646 B1 * | 5/2002 | Ringermacher | ....... | G01B 11/06 250/330 |
| 7,220,966 B2 * | 5/2007 | Saito | ...................... | G01N 25/72 250/341.1 |

(Continued)

FOREIGN PATENT DOCUMENTS

| | | |
|---|---|---|
| DE | 102006043339 B4 | 11/2010 |
| EP | 1203224 B1 | 7/2008 |

(Continued)

OTHER PUBLICATIONS

Sekagami et al., "Application of pulse heating thermography and lock-in thermography to quantitative nondestructive evaluations", Infrared Physics and Technology 43, 2002, pp. 211-218.*

(Continued)

*Primary Examiner* — Reza Aghevli
(74) *Attorney, Agent, or Firm* — Klarquist Sparkman, LLP (57) ABSTRACT

The invention provides a method for a non-destructive, non-contacting and image forming examination of a sample by means of heat flow thermography. The method comprises exciting the sample at least twice independently from each other by means of the heat pulses from the excitation source; taking a first thermal image of the surface of the sample at a first time distance $\Delta t_1$ from a first triggering of the heat pulse which first time distance $\Delta t_1$ is characteristic for gradients in heat flow velocity in a first depth below the surface of the sample; taking a second thermal image of the surface of the sample at a 1 second time distance $\Delta t_2$ from a second triggering of the heat pulse which second time distance $\Delta t_2$ is characteristic for gradients in heat flow (Continued)

velocity in a second depth below the first depth; and taking any thermal images of the surface of the sample at a further time distances $\Delta t_n$ from any subsequent triggering of the heat pulse which further time distances $\Delta t_n$ are characteristic for gradients in heat flow velocity in further depths lying deeper as the second depth; and extracting from the thermal images an indication of the presence of any gradients of heat flow velocity at the respective depth distances from a surface of the sample. The system is configured to carry out the above method.

15 Claims, 7 Drawing Sheets (51) Int. Cl.
  G06K 9/52      (2006.01)
  G06T 7/20      (2017.01)
  H04N 5/33      (2006.01)
  H04N 5/243     (2006.01)
  G06T 7/00      (2017.01)
  G01J 5/00      (2006.01)
(52) U.S. Cl.
  CPC ........... *G06T 7/0004* (2013.01); *H04N 5/243* (2013.01); *H04N 5/33* (2013.01); *G01J 2005/0077* (2013.01); *G01J 2005/0081* (2013.01); *G06T 2207/10048* (2013.01)

(56) References Cited

U.S. PATENT DOCUMENTS

| | | | | |
|---|---|---|---|---|
| 8,204,294 | B2* | 6/2012 | Alloo | G01N 25/72 382/141 |
| 8,577,120 | B1* | 11/2013 | Koshti | G06T 7/0004 250/341.8 |
| 9,066,028 | B1* | 6/2015 | Koshti | H04N 5/33 |
| 2003/0137318 | A1* | 7/2003 | Enachescu | G01R 31/308 324/760.01 |
| 2005/0008215 | A1* | 1/2005 | Shepard | G01N 25/72 382/141 |
| 2005/0056786 | A1* | 3/2005 | Shepard | G01N 25/72 250/341.4 |
| 2006/0062561 | A1* | 3/2006 | Shepard | G03B 41/00 396/155 |
| 2010/0033565 | A1* | 2/2010 | Benzerrouk | G06T 7/0004 348/125 |
| 2010/0091812 | A1* | 4/2010 | Louban | B23K 11/36 374/4 |
| 2010/0163732 | A1* | 7/2010 | Louban | G01N 25/72 250/341.6 |

FOREIGN PATENT DOCUMENTS

| | | |
|---|---|---|
| EP | 2743688 A1 | 6/2014 |
| JP | 2011-122859 A | 6/2011 |
| JP | 2015-500476 | 1/2015 |
| RU | 2343465 C1 | 1/2009 |
| WO | WO 2013083846 | 6/2013 |
| WO | 2014/095170 A1 | 6/2014 |

OTHER PUBLICATIONS

Maldague, Xavier P.V., "Theory and Practice of Infrared Technology for Non-destructive Testing", John Wiles & Sons, Inc., Apr. 2001, pp. 527-536.

International Search Report and Written Opinion for PCT/EP2013/073757 dated Jan. 28, 2014.

Notice of Reasons of Refusal (w/ English translation) for related Japanese Application No. JP2015-546914, dated Oct. 24, 2017, 7 pages.

* cited by examiner

METHOD AND SYSTEM FOR THE EXAMINATION OF A SAMPLE BY MEANS OF THERMOGRAPHY

RELATED APPLICATIONS

The present application is the national phase of International Application No. PCT/EP2013/073757, filed on Nov. 13, 2013, which claims the benefit of priority to European Patent Application No. 12197611.2, filed on Dec. 17, 2012, and the disclosures of which are hereby incorporated herein by reference in their entireties.

The invention relates to a method and a system for the non-destructive, non-contacting and image forming examination of a sample by means of heat flow thermography where the examination consists of evaluating the presence of any gradients in heat flow velocity at respective depth distances from a surface of the sample, wherein the sample is excited by heat pulses of at least one excitation source, and thermal images of a thermal flow originating from the heat pulses is captured by at least one infrared camera, and wherein the thermal images are evaluated by means of signal and image processing and depicting a thermal flow with a resolution in time and in space.

A non-destructive and non-contacting measurement of physical thermal characteristics of a layered material can for example be carried out with the aid of a punctual laser excitation as well as a plurality of punctual detectors (RU 2343465 C1). Therein, the laser beam source as well as the detectors are to be moved along the surface of the material to be inspected in order to ensure a surface covering measurement. This method is, however, also not adapted to keep pace with an industrial fabrication.

Besides the known nondestructive methods for evaluating the layer structure of a layered material, as for example methods using ultra sound, a magnetic field and an eddy current, the active heat flow thermography has been established in the last years for a imaging measurement method. The procedures implemented with this method are based on the evaluation of the heat transport through the material to be measured as a function of the surface temperature in transmission or reflection. The generated heat flow is excited by single energy pulses or by periodically repeating energy pulses and is than captured by means of an infrared camera in a sequence of images. From the analysis of the pixel related gradients in heat flow velocity, a characteristic value is extracted (for example by a Fourier transformation or lock-in-correlation) which describes the behavior in time of the heat wave through the layer system and which is correlated to a layer thickness value evaluated by other, destructive or contacting methods ("Theory and Practice of Infrared Technology for Non-destructive Testing", Xavier P. V. Maldague, John Wiles & Sons, Inc., 2001). As a pulse like excitation in such a method, a flash (EP 1 203 224 B1) or a short application of a heating or cooling gas, respectively, can be used (DE 10 2006 043 339 B4).

The heat flow thermography has been established in the past years as a non-contacting and nondestructive examination method. According to this method, a sample is excited by at least one source in order to generate a heat flow. The heat radiation immediate from the sample is captured by at least one infrared camera in a sequence of images, and is passed on to a calculating unit. Resulting images of various types can be generated in the computing unit whereby a thermal image or an amplitude- or phase image, respectively is retrieved (Theory and Practice of Infrared Technology for Nondestructive Testing, Xavier P. V. Maldague—John Wiley & Sons, Incl., 2001).

The method for examining a joint connection by thermography is described in DE 10 2001 120 808.2 wherein an imaging, time and local high resolution is provided which is scalable in both parameters examination of a joint connection (for example resistance weld point or laser weld seam) out of such thermally thin layers. Thereby, for example a weld lens in a resistance weld point to be examined can be differentiated from its near surroundings (welding adhesive). In this context, intensity variations of the excitation source, the state and the characteristics of the material surface as well as the thickness of the material are not supposed to influence substantially the measurement result. Therefore, a resulting image is to be used which does not represent an absolute value of the heat flow or its velocity, respectively, through the weld connection to be examined, but rather a corresponding local velocity difference of the heat flow. Such a resultant image can for example be generated by the infrared lock-in thermography wherein a so-called phase image is generated (Theory and Practice of Infrared Technology for Nondestructive Testing, Xavier P. V. Maldague, John Wiley & Sons, Inc., 2001). Such a phase image shows the run time of thermal waves in the material assembly. Thereby, the heat conductivity differences between different image points of the material connection to be examined become visible.

The geometrical resolution of a measurement system may be extended, therein, by means of high resolution cameras and respective objective lenses, respectively, almost arbitrarily. The maximum time resolution is, however, fixedly defined by the camera system. The image repetition rates achievable by modern detector matrices of infrared cameras when using all presently available decoder elements (full image mode=640×512 pixels for example) are in the range of 100-200 images per second. This is not sufficient in order to resolve the thermal answer signals of thinner layers or of layers out of thermally fast materials which form the so-called thermally thin layers.

US 2005/056786 A1 discloses a pulse controller device for controlling the excitation of a heat source used in thermographic imaging is disclosed. The pulse controller device comprises a power supply, a heat source coupled to the power supply, a device coupled to the power supply signaling the power supply to deliver electrical power to the heat source, a sensor for sensing the delivery of electrical power to the heat source, a flash duration module coupled to said sensor for measuring a duration of time, and a gate device coupled to said flash duration module for gating the electrical power utilized by the heat source. A method for thermographically evaluating a sample is also disclosed.

US 2005/008215 A1 relates to a method for compiling thermographic data including obtaining data indicative of a monotonically changing characteristic of a specimen, sequencing the data or a surrogate of the data into a plurality of groups, categorizing, within each group, the frequency distribution of an attribute of the data or an attribute of said surrogate data, and compiling, from one or more groups, a collection of two or more of the frequency distributions.

US 2003/137318 A1 describes methods and systems for providing improved defect detection and analysis using infrared thermography. Test vectors heat features of a device under test to produce thermal characteristics useful in identifying defects. The test vectors are timed to enhance the thermal contrast between defects and the surrounding features, enabling IR imaging equipment to acquire improved thermographic images. In some embodiments, a combination of AC and DC test vectors maximize power transfer to expedite heating, and therefore testing. Mathematical transformations applied to the improved images further enhance defect detection and analysis. Some defects produce image artifacts, or "defect artifacts," that obscure the defects, rendering difficult the task of defect location. Some embodiments employ defect-location algorithms that analyze defect artifacts to precisely locate corresponding defects.

According to US 2010/163732 A1, in a method for the automatic inspection of a welding seam using heat flow thermography, a feature vector is established which represents a time course of a detected heat flow. The feature vector is used to determine, from a series of thermal images, a first characteristic thermal image, which corresponds to a minimum heat flow through an object to be examined, and a second characteristic thermal image, which corresponds to a maximum heat flow through the object, wherein a heat flow directly from an excitation source has already dissipated. A suitable thermal image is used from the series of thermal images to detect and evaluate the welding seam in relation to defects of various defect types, for each defect type, the characteristic thermal images being used as references to determine the respective suitable thermal image.

At present, this is attempted to be achieved by a large restriction of the sensitive detector surface (partial-image-mode), for example 16×16 pixel, which, however, has the consequence of the loss of the geometrical resolution and, in spite of that, cannot ensure a sufficient resolution in time. The modern layered material consists mostly of such so-called thermally thin layers. Therefore, the examination of the total layer structure of a layered material with high time and local resolution is of exceptional economical and technical importance.

In terms of finding surface near defects as early as possible in the production line one has to prevent faulty parts from high values added. Thus bubbles, cavities, cracks and similar defects are to be detected in the raw parts before further mechanical processing is performed. Therefore the examination of surfaces of casting parts with high time and local resolution is of exceptional economical and technical importance.

Starting from this, it is the object of the invention to provide a method and a system for a non-destructive, non-contacting and image forming examination of a sample by means of heat flow thermography where the examination consists of evaluation a presence and/or depth distance values of any time gradients heat flow velocity (defects) from a surface of the sample with high time and local resolution.

For this purpose, the method of the invention comprises the features of claim 1. This method allows the required resolution of the thermal image since a full frame camera (for example a camera having 640×512 pixels) can be used while the time distances $\Delta t_n$ are selected such that the thermal images are taken with a nearby infinite virtual frame rate of up to at least 10000 frames per second. With such a virtual frame rate, a high speed heat flow dissipation of the sample can be accounted for even if the heat dissipation process, depending on the material of the sample, takes between 0.5 and 5 ms or between 5 and 50 ms only with a sample made of aluminum, copper or steel, respectively. The whole measurement process can be completed within a very short period of time, i.e. within less than 2 s. for each sample.

In other words, the useful thermal images to be considered are taken in several loops where each loop consists of the triggering of the excitations pulse, recording at least one thermal image to further be considered, and of recording which is also the end of the loop.

According to a preferred embodiment of the method of the invention the time distances $\Delta t_n$ are independently adjustable in this way, any desired virtual frame rate can be established by an appropriate selection of the time distances $\Delta t_n$.

According to a preferred embodiment of the method of the invention the time distances $\Delta t_n$ are selected from a model of the gradient in the heat flow velocity in the sample. Since the model can be tailored to the requirements of a particular sample, for example to the requirements present in a piston casted of aluminum or steel, the time distances for this particular sample can easily be set in a way to receive the required results, i.e. a clear picture of the presence and depths of a gradients in heat flow velocity (defect in the sample).

According to a preferred embodiment of the method of the invention the method further comprises taking a first sequence of thermal images including the first thermal image; taking a second sequence of thermal images including the second thermal image of the surface of the sample; and taking further sequences of thermal images including further thermal images of the surface of the sample. This allows to extend the range of usable infrared cameras with semiconductor detection matrices by cameras which are configured to take sequences of thermal images in addition to cameras which are configured to take only one image per loop. In this case, it is possible to select the first image of each sequence in each loop as the useful thermal image to be further considered in the examination of the sample and to correlate this first image with images recorded later on in a defined time distance within the same loop.

According to a further preferred embodiment of the method of the invention the image intensity of each of the captured images is corrected so that all captured images have the same intensity offset; or the image intensity of each of the captured image sequences is corrected so that all captured image sequences have the same intensity offset. This ensures that the intensity values which are derived locally from the same positions but are from different excitations are corrected to be comparable in the areas to be evaluated and can, therefore, be processed mathematically unambiguously.

According to a further preferred embodiment of the method of the invention one of the captured images is used as a reference image for correcting the image intensity in the rest of the captured images; or one of the captured image sequence is used as a reference sequence for correcting the image intensity in the rest of the captured image sequences. Thereby, the same intensity of said is ensured for all captured images.

According to a further preferred embodiment of the method of the invention the first captured image is used as a reference image for correcting the image intensity in the rest of the captured image sequences; or the first captured image of another sequence is used as a reference image for correcting the image intensity in the rest of the captured images. Thereby, the rest of the images can be already used with a correction for the further processing.

According to another aspect of the invention a method is provided wherein the sample comprises a substrate or a work piece including defects close to a surface of the sample which defects are observed due to gradients in heat flow velocity of the heat flow from the surface of the sample into a body, wherein the indication of presence and/or depth distance of a particular defect is a hot spot in a respective image which was taken at a time distance from the excitation of the sample related to the depth distance of the defect from the surface of the sample.

According to another aspect the invention provides a system according to claim 12.

According to a preferred embodiment of the system of the invention the controller is further configured to independently adjust the time distances $\Delta t_n$.

According to a further preferred embodiment of the system of the invention the controller is further configured to select the time distances $\Delta t_n$ from a model of the gradients in heat flow velocity in the sample, the model being stored in the controller.

According to a further preferred embodiment of the system of the invention the controller is further configured to control the camera to take a first sequence of thermal images including the first thermal image; to take a second sequence of thermal images including the second thermal image of the surface of the sample; and to take further sequences of thermal images including further thermal images of the surface of the sample.

As is apparent from the above specification, the method and the system of the invention are applicable in cases where a gradient in heat flow velocity in a sample or substrate is to be detected where the changes in time of the heat flow dissipation curve or the intensity curve of the thermography curve varies so fast that a full range camera, for example a camera having 640×514 pixel full frame, can not record the changes in the intensity in the image of the heat flow. In other words the method of the invention is applicable in cases where the speed of the camera, i.e. the number of frames that can be taken per second, is to slow to capture the changes of the intensity in the image of the heat flow. For example a camera having 640×512 pixel full frame has a speed of 200 frames per second whereas a frame rate of 2000 frames per second or even more then 4000 frames per second is desired in the case of the examination of the above mentioned samples having defects next to their surface. In such cases, the thermal images can be used in order to find an indication of the presence of any gradients in heat flow velocity at the respective depth distances from a surface of the sample. Since the time distances $\Delta t_n$ can be selected independently from each other, any desired virtual time resolution of the recording of the heat flow can be achieved.

Embodiments of the invention further comprise any methods or systems described above wherein the recording of images or sequences starts not with the shifted trigger after flash. Those terms of description are only used to describe the basic mechanism containing the principle functionality. In here the recording starts before the flash is released and any one of the following frames is the first frame useful for the purpose of the invention in terms described before and after this chapter.

Further advantages, features and potential applications of the present invention may be gathered from the description which follows, in conjunction with the embodiments illustrated in the drawings.

Throughout the description, the claims and the drawings, those terms and associated reference signs will be used as are notable from the enclosed list of reference signs. In the drawings FIG. 1 schematically shows a system for capturing the respective total heat flow processes in reflection of a sample according to an embodiment of the invention;

Figure 1:
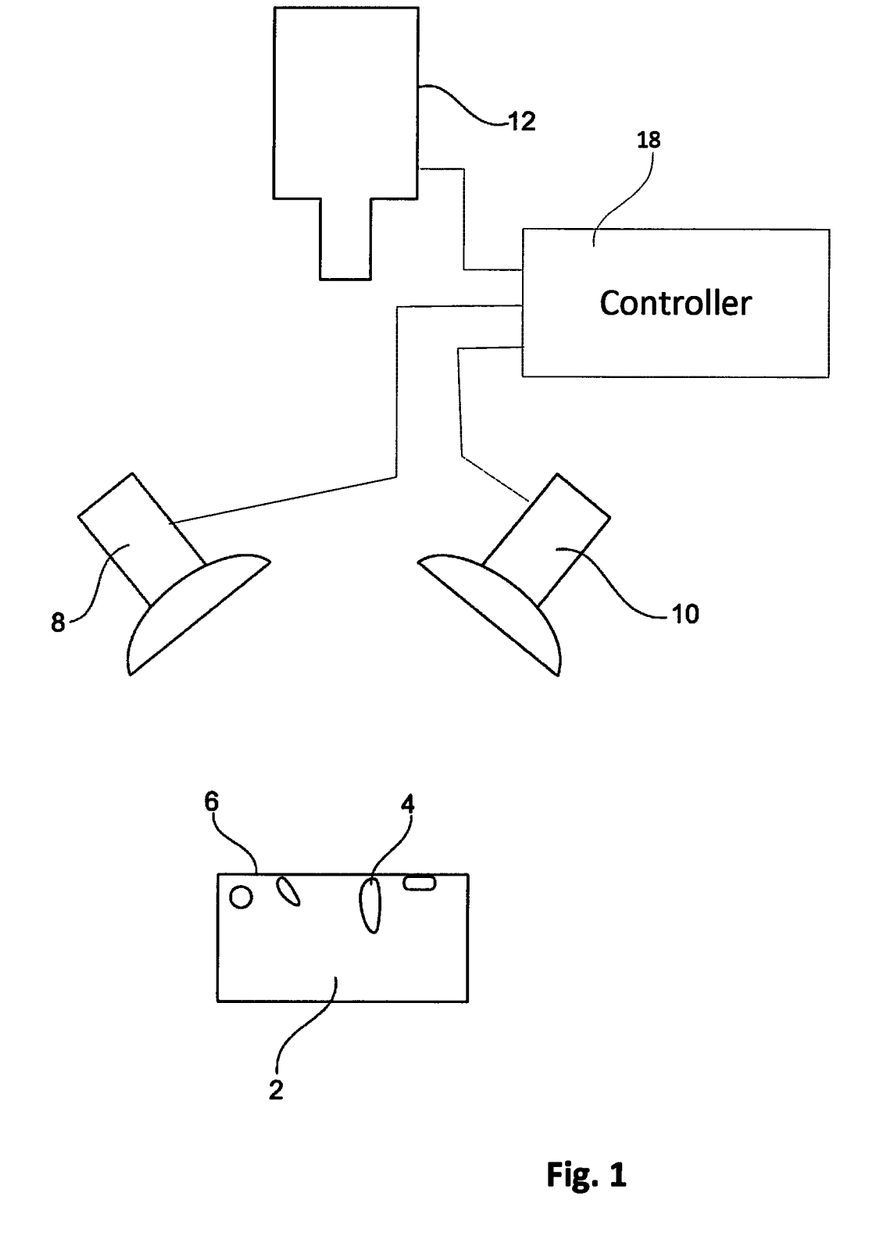

FIG. 1 schematically shows a system for capturing the respective total heat flow processes in reflection of a sample 2 having a pore 4 which as a rule contains air as an example of a defect. The sample can be a metal substrate, a semiconductor substrate or a top surface of a construction component. A surface 6 of the substrate 2 is excited by flash pulses of two flash lights 8, 10, and a camera 12 is directed to the sample 6 to take thermal images of the surface during the heat dissipation following an excitation by the flash lights 8, 10.

Figure 2:
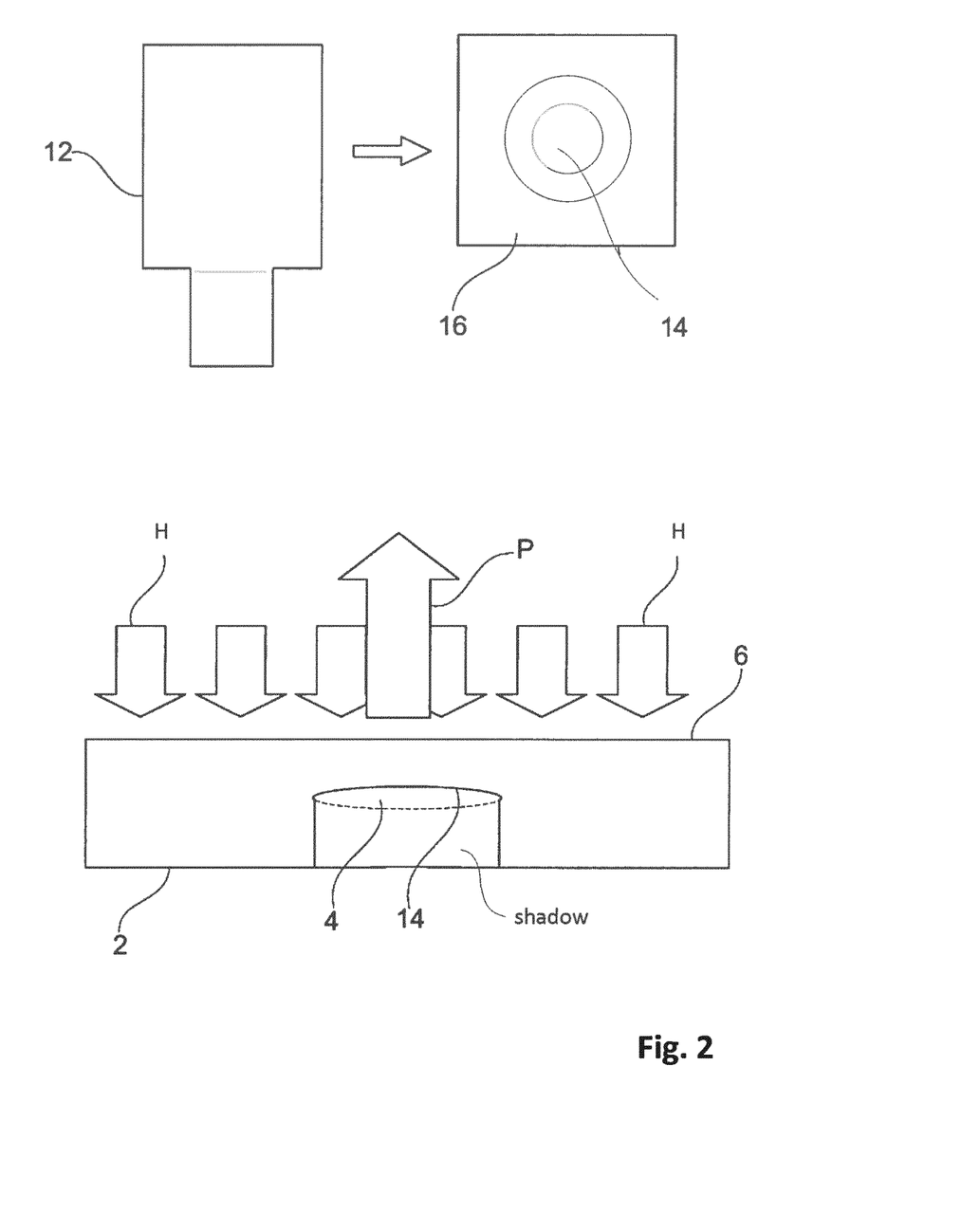
FIG. 2 schematically shows the principle of taking thermal images showing a defect form a sample.

FIG. 2 shows the application of the method of the invention on the sample 2 which is a work piece, for example a piston out of copper or aluminum and which has the pore 4. The sample 2 can also be a metal substrate, a semiconductor substrate or a top surface of a construction component as long as the sample has a high heat flow velocity characteristic. The substrate 2 is heated up again by the flash lights 8, 10 shown in FIG. 1 in a pulsed manner, as indicated by the arrows H. If heated in this way, the pore 4 is an obstacle to the heat flow in the substrate starting from the surface 6 of the sample and directed into the sample 2 (from top to bottom in FIG. 2).

The pore 4 is an obstacle to the heat flow because of the disturbed heat flow velocity from the substrate 2 to the pore 4 in the sense of a built up gradient. At the pore 4, the heat flow inside the sample is interrupted thus it has to decay by a motion sideward (as viewed in FIG. 2) and creates a hot spot 14 the shape of which reflects the shape of the pore 4 added the effect of dissipation of the heat sideways in the sample 2 as viewed in FIG. 2. An image 16 of the hot spot 14 and the rest of the surface of the substrate is captured along the line of the arrow P by a camera 12. The camera 12 issues the image 16 where the hot spot 14 produced by the pore 4 is clearly visible.

Since the instance in time when the hot spot 14 is created by the heat flow reflected from the pore 4 depends on the distance between the upper border of the pore 4 from the surface 6 of the sample 2, the image of the pore 4 appears in an image which is delayed with respect to the excitation flash by the runtime of the heat flow between the pore 4 and the surface 6. Therefore, in the case of various defects like the pore 4 in different depths of the substrate will appear in images at different time distances from the excitation flash. By taking and evaluating the images in the manner described above, one can not only verify the existence of the any pores in the substrate 2 but also the depths locations of the respective defects by correlating the time delay of their respective images from the triggering of the excitation flash.

As long as the respective intensity values of the captured images are not corrected, they show an increased resolution in time of the evaluated pixel related functions of the surface intensity, but they cannot be processed mathematically in an unambiguous way. In the correction, the first image serves as a reference and all captured images are subject to the same intensity offset. Therefore, the thermal images are corrected so that all captured images have the same intensity offset, or the image intensity of each captured image sequence is corrected so that all captured image sequences have the same intensity offset. Furthermore, one of the captured images is used as a reference for correcting the image intensity in the rest of the captured image sequences, or the first captured image is used as a reference image for correcting the image intensity in the rest of the captured images. Thereby, the respective intensity values of the captured images are corrected.

Referring back to the FIG. 1 and FIG. 2, the system of the invention comprises a signal and image processing controller 18 including a display. The controller 18 is connected to the excitation source 8 or the excitation sources 8, 10 to control the excitation sources 8, 10 to excite the sample 2 at least twice independently from each other by means of the heat pulses, The controller 18 is also connected to the camera 12 to control the camera to capture thermal images of a thermal flow originating from the heat pulses from the excitation sources 8, 10. The processor of the controller 18 is configured to evaluate the thermal images and to depict a thermal flow resolution in time and in space. The controller 18 is further configured to control the camera 12 to take thermal images of the surface of the sample 2 at time distances $\Delta t_n$ from triggering of any subsequently triggered heat pulses which time distances $\Delta t_n$ are characteristic for gradients in heat flow velocity in respective depth distances below the surface of the sample 2. From the thermal images, an indication of the presence of any gradients in heat flow velocity at the respective depth distances from a surface of the sample 2 is extracted by the controller 18.

In particular, the controller 18 is further configured to independently adjust the time distances $\Delta t_n$. Preferably, the controller 18 is further configured to select the time distances $\Delta t_n$ from a model of the gradients in heat flow velocity in the sample 2, the model being stored in the controller 18.

In an embodiment of the invention, the controller 18 is further configured to control the camera 12 to take a first sequence of thermal images including the first thermal image; to take a second sequence of thermal images including the second thermal image of the surface of the sample 2; and to take further sequences of thermal images including further thermal images of the surface of the sample 2.

Figure 3:
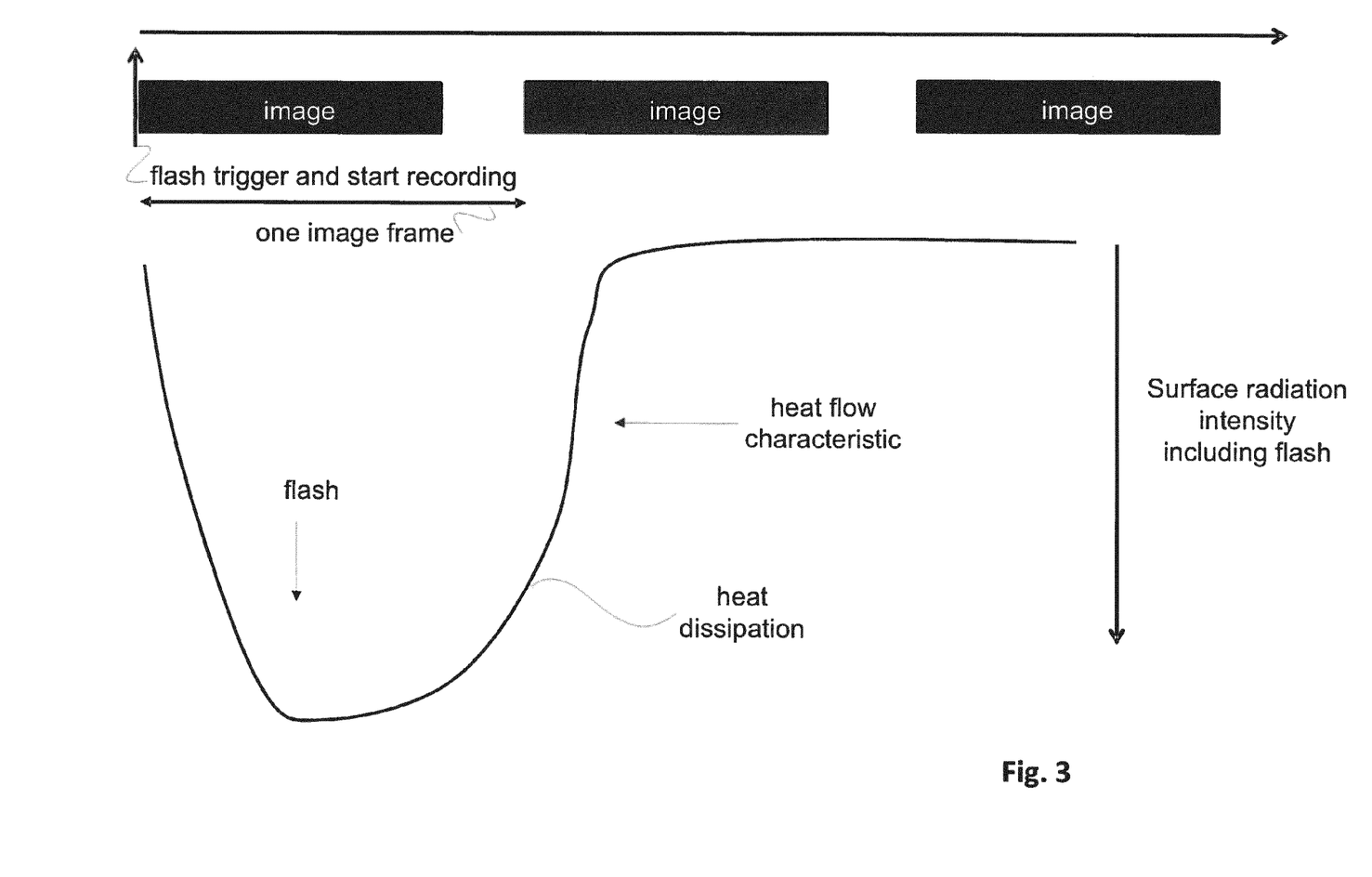
FIG. 3 schematically shows the timing of capturing images with a frame rate of a conventional infrared camera.

In the following, the background of the present invention is explained with respect to FIG. 3 which schematically shows the timing of capturing images with a frame rate of a conventional infrared camera. FIG. 3 shows three images of a sequence of images taken by the infrared camera, for example at a frame rate of 200 frames per second. Considering the timing of the images with respect to the heat flow characteristic on the surface of the sample which starts with the flash excitation and quickly decreases from the flash excitation to the equilibrium temperature within 0.5 to 5 ms as stated above. Since the useful thermal images have to be taken during the heat dissipation portion of the heat flow characteristic, it is immediately apparent from FIG. 3 that the ordinary frame rate of 200 frames per second of a conventional infrared camera is not adapted to analyze the presence and depths distribution of any defects in any sample.

Figure 4:
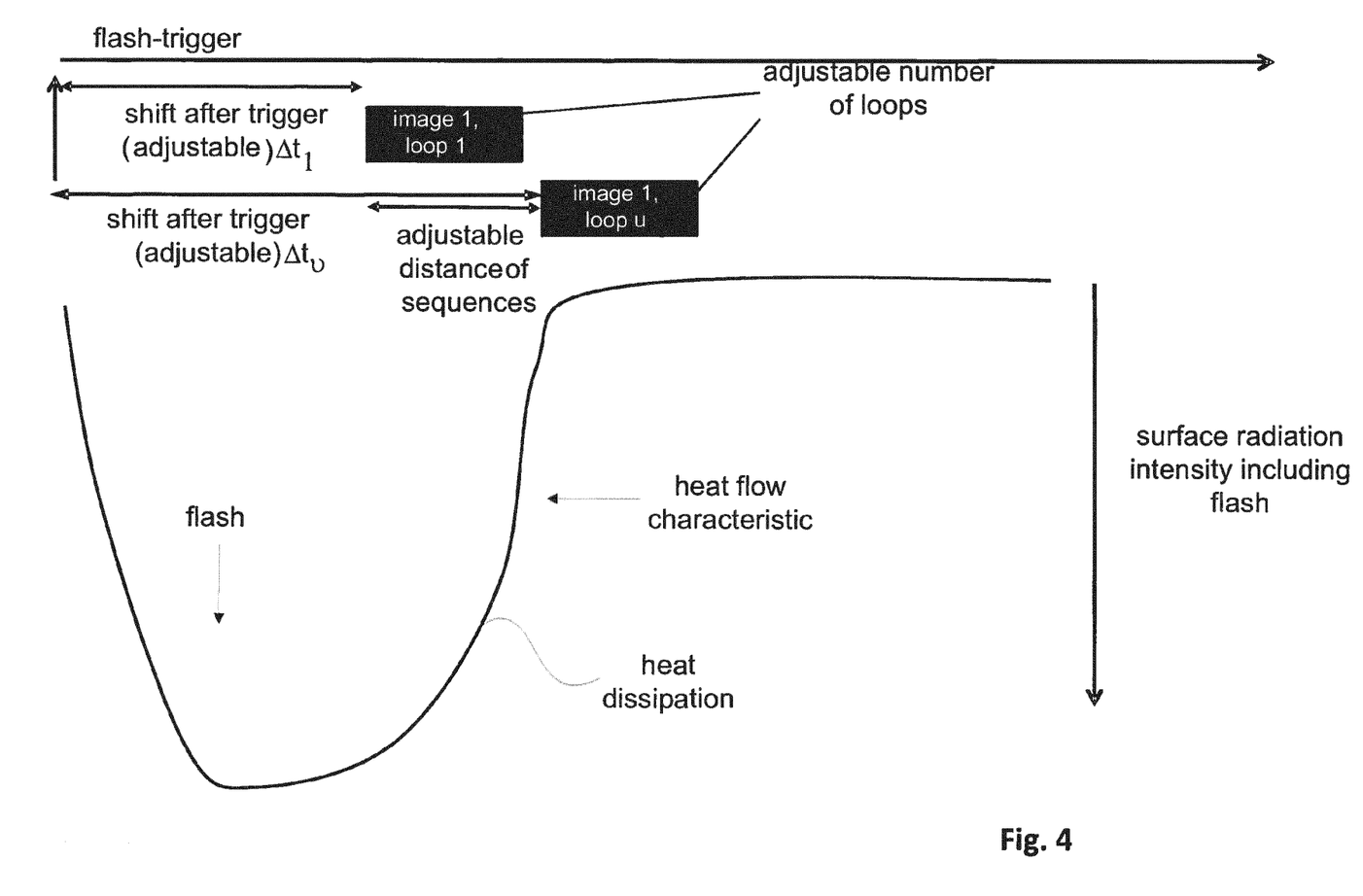
FIG. 4 schematically shows the timing of capturing image sequences with the time delays of the individual thermal images being individually adjusted.

FIG. 4 schematically shows the timing of capturing images where the time delays of the individual thermal images with respect to the triggering of the flash can be individually adjusted. The shift after trigger $\Delta t_1$ of image 1 can for example be adjusted such that the image 1 is taken at an instance of time of 0.5 ms after flash where the hotspot appears of a defect being located 220 µm below the surface of a sample 2 created of aluminum or 8.2 µm below the surface of the sample 2 in case of a sample of steel, as will be explained later in more detail.

As can be seen from FIG. 4, image 1 of loop 2 is delayed with respect to the flash trigger by $\Delta t_2$ where the time difference $\Delta t_2$ is adjustable for example by adjusting the distance of sequences, i.e. the distance $\Delta t_2 - \Delta t_1$ by which the starting point of image 1 of loop 1 to image 1 of loop 2 is deferred. In case a further time resolution of the heat dissipation portion of the heat flow characteristic is required, further images can be taken in further loops by adjusting the time difference $\Delta t_n$ to capture images of defects located in depths in between the depths captured by the image 1 of loop 1 and of the image 1 of loop 2. Since the number of loops is adjustable, any number of loops can be set in order to differentiate between defects located in different depths within the sample.

Figure 5:
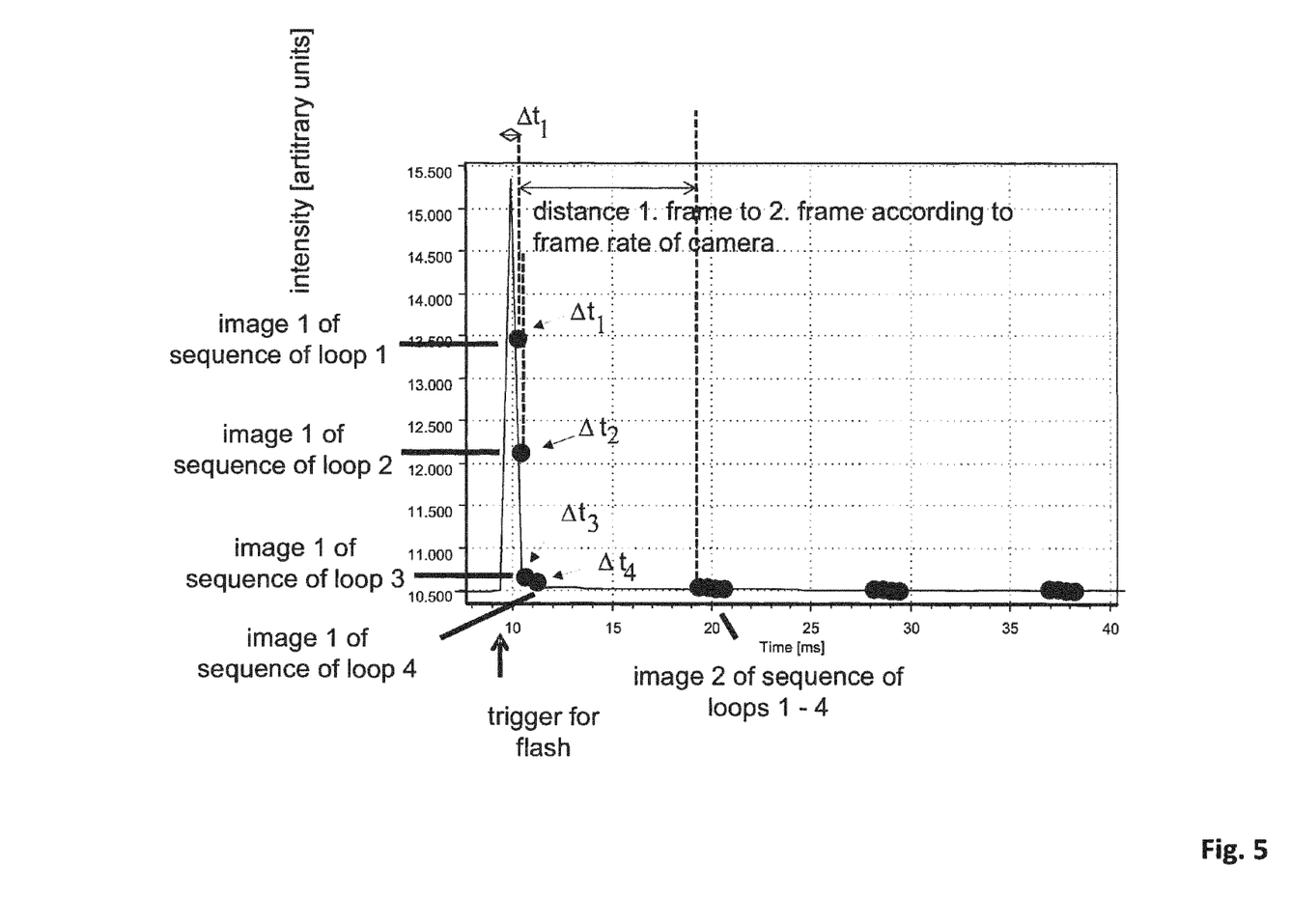
FIG. 5 schematically shows the timing of captured image sequences with the time delays of the individual thermal images being individually adjusted.

FIG. 5 schematically shows the timing of captured image sequences with the time delays of the individual thermal images being individually adjusted. In FIG. 5, the intensity of the heat radiation development seen by the camera is plotted in arbitrary units against the time in Milliseconds. As obvious, image 1 of the sequence of loop 1 is delayed by $\Delta t_1$, image 1 of the sequence of loop 2 is delayed by $\Delta t_2$, image 1 of the sequence of loop 3 is delayed by $\Delta t_3$ and the image 1 of the sequence of loop 4 is delayed by $\Delta t_4$. Furthermore, it is obviously visible that the time difference between the delay $\Delta t_1$ and delay $\Delta t_4$ is only about 3 ms (i.e. the virtual frame rate of the camera mentioned in the invention is very short with respect to the normal frame rate of the camera) whereas the second images of the sequences of the loops 1-4 are apart almost by 10 ms which again shows that it is not possible to provide the required time resolution by an ordinary infrared camera.

Figure 6:
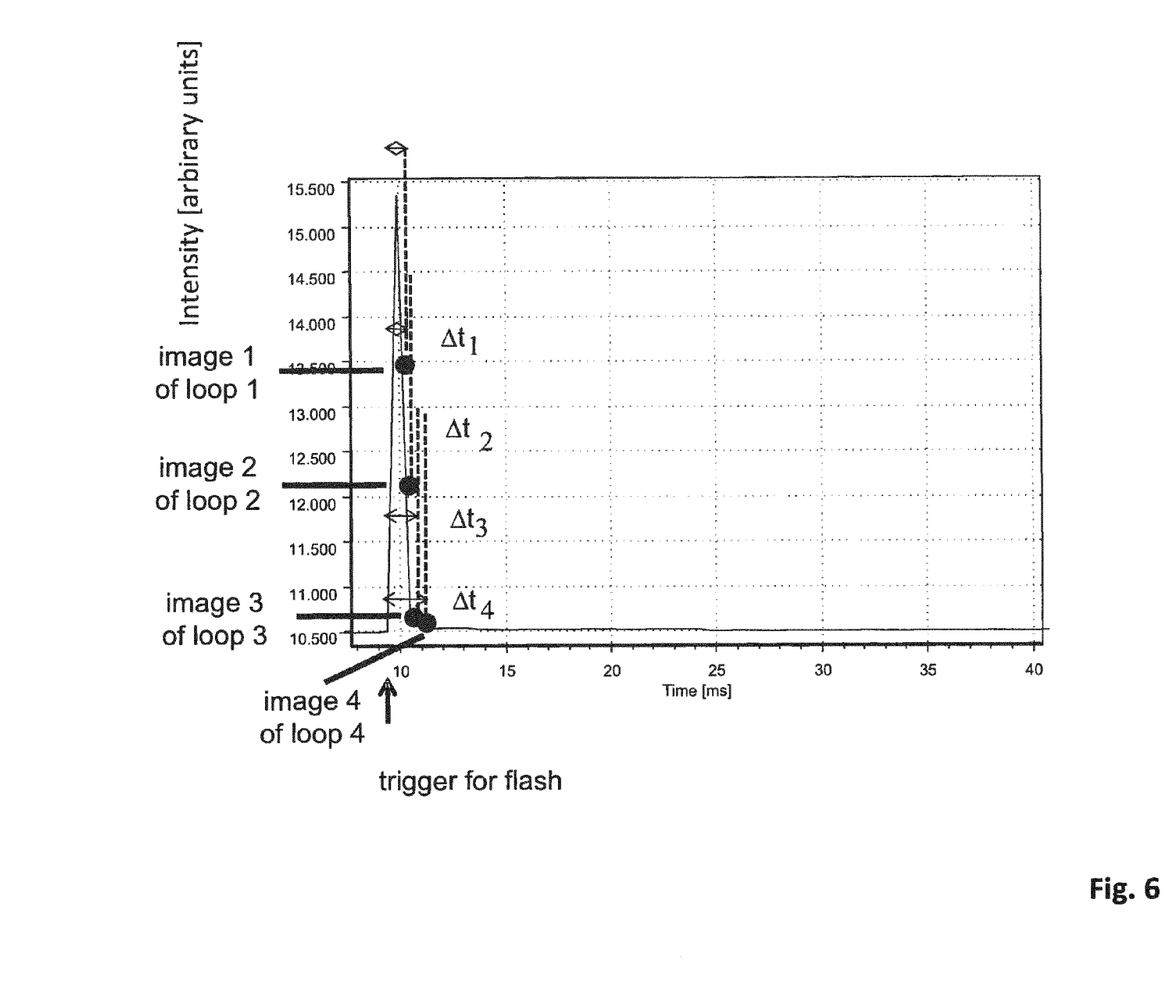
FIG. 6 schematically shows the timing of captured single images with the time delays of the individual thermal images being individually adjusted.

FIG. 6 schematically shows the timing of captured thermal images with the time delays of the individual thermal images being individually adjusted. FIG. 6 is very similar to FIG. 5 with the exception that the camera is configured to take single images and no sequences as it was the case in FIG. 5. This can serve to further reduce the time needed for examining a sample image recording loops 1-4 are shorter compared to recording of sequences of at least two images in each loop.

Figure 7:
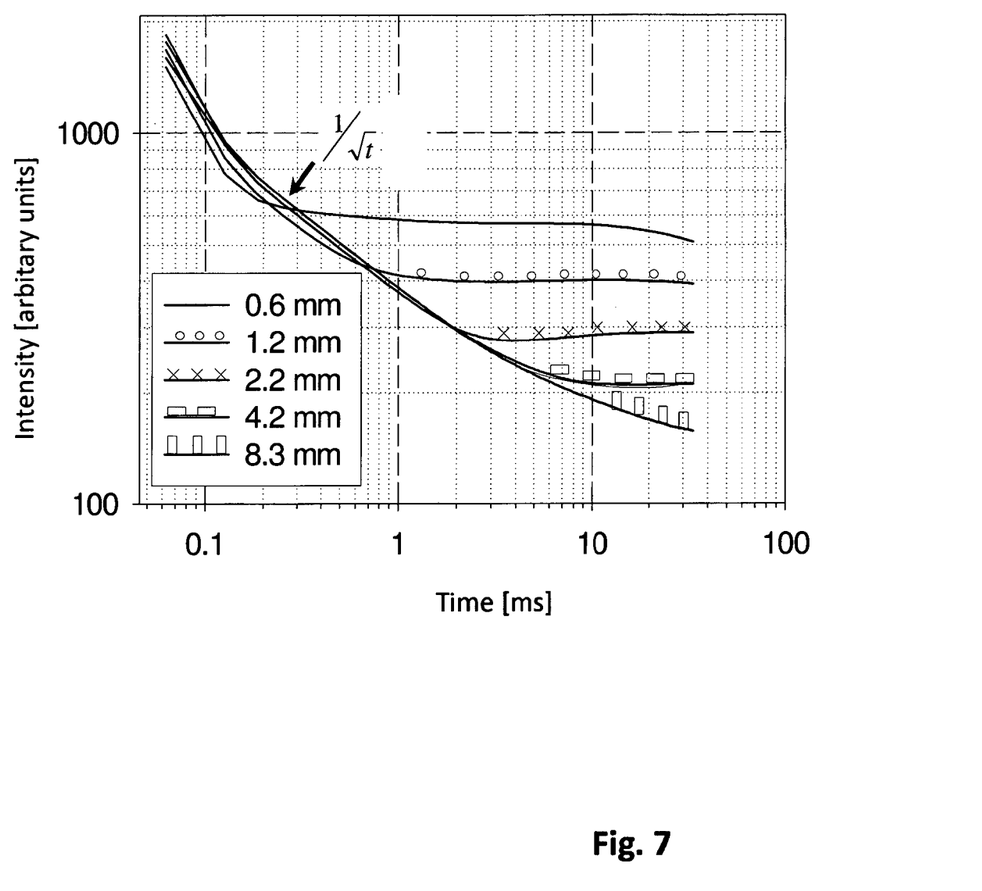
FIG. 7 shows characteristic curves of the intensity versus the time of the heat flow after an excitation.

FIG. 7 shows an example of characteristic curves of the surface intensity versus the time of the heat flow after excitation where this curve is used as model for selecting the time distances $\Delta t_n$ with respect to a particular sample, for example a piston out of aluminum or a piston out of steel.

The graph of FIG. 7 is based on a sample of a piston out of steel. The parameter of the five curves shown is the depths of any defects within the sample at a depth of 0.6 mm, at a depth of 1.2 mm, at a depth of 2.2 mm, at a depth of 4.2 mm and a depth of 8.3 mm, respectively. The distance from the surface of the sample to the defect is related to the time (runtime of the heat flow) by the relationship that the depth is proportional to t. Therefore, in case a defect is at a depth of 0.6 mm below the surface of the sample, the useful image has to be taken 0.2 ms after the triggering of the flash, i.e. at an instant of time where the curve with the parameter 0.6 mm leaves the bundle of curves where the curves are running substantially parallel to each other. For a depth of 1.2 mm, the respective time delay would be about 0.8 ms. The time delay for the curve with the parameter 2.2 mm would be about 2 ms, and the time delay of the curve with the parameter of 4.2 mm would be about 4 ms, whereas defects in a depth of 8.3 mm can no longer be verified.

The duration of the heat spot depends vice versa on the heat gradient applied. This is built up by the defect. Therefore the absolute applied heat and the size of defect give, the probability to visualize surface near defects later on when you detect more deep lying defects.

In another example, where the sample is a piston made of aluminum, depths of the defects below the surface of the sample of 0.22 mm, and 0.32 mm and 0.70 mm correspond, respectively, to time delays of 0.5 ms, 1 ms and 5 ms. Therefore, the time delays are different for different materials of the sample. However, the principle to adapt the time delays of taking the useful pictures are adapted to the depths of the defects in the sample is applicable for any materials.

It is apparent from the above specification that the invention is not restricted to the application in the two cases which have been disclosed as examples. Rather, the method of the invention is applicable in all cases where the speed (frames per second) of the camera is insufficient to produce the image sequences required for locating the existence and/or the depths location of any gradients in heat flow velocity, such as border surfaces between layers of different flow velocity characteristics as well as defects, like holes, pores and cuts in a substrate or a work piece.

LIST OF REFERENCE SIGNS 2 sample
4 pore
6 surface
8 flash light
10 flash light
12 camera
14 hot spot
16 image
18 controller

The invention claimed is:

1. A method of heat flow thermography, comprising:
selecting a first time interval and a second time interval based on model heat flow gradients associated with a sample at a first depth from a sample surface and a second depth from the sample surface, respectively;
exciting the sample with a first heat pulse and a second pulse from at least one excitation source;
capturing a first thermal image and a second thermal image of a surface of the sample responsive to the first heat pulse and the second heat pulse, respectively, with at least one infrared camera, wherein the first thermal image is captured at the first time interval from the excitation of the sample with the first heat pulse and the second thermal image is captured at the second time interval from the excitation of the sample with the second heat pulse; and
evaluating the first thermal image and the second thermal image with a signal and image processing system so as to;
and
indicate a presence of a gradient in heat flow velocity at the first depth and the second depth.

2. The method of claim 1, further comprising selecting a plurality of time intervals associated with respective depths, applying associated excitation pulses, capturing images at each of the associated time intervals, and indicating a presence of respective gradients in heat flow velocity at each of the depths.

3. The method of claim 1, wherein the capturing the first thermal image and the second thermal image includes capturing a first sequence of thermal images at the first time interval from the excitation of the sample and a second sequence of thermal images at the second time interval from the excitation of the sample.

4. The method of claim 3, further comprising adjusting an image intensity value associated with ef each of the first and second captured image sequences by a common corrective intensity offset.

5. The method of claim 1, wherein each of the thermal images is corrected with a common intensity offset.

6. The method of claim 3, further comprising selecting a captured image of the first sequence of the second sequence and adjusting the image intensity in the other captured images of the first sequence and the second sequence based on the selected captured image.

7. The method of claim 6, wherein the selected captured image is the first captured image in either the first sequence or the second sequence.

8. The method of claim 3, wherein one of the first and second captured image sequences is used as a reference sequence for adjusting the image intensity of the other of the first and second captured image sequences.

9. The method of claim 8, wherein the first captured image sequence is used as a reference for correcting the image intensity of the second captured image sequence.

10. The method of claim 1, wherein the sample includes at least one defect proximate the surface of the sample and associated with heat flow from the surface of the sample into an interior of the sample, wherein
the indication of the presence of a particular defect corresponds to a hot spot in at least one image captured at a time interval associated with a depth of the defect from the surface of the sample.

11. A system for heat flow thermography, comprising:
a camera;
at least one excitation source configured to excite a sample with heat pulses; and
a signal and image processing controller configured to:
select a first time interval and a second time interval based on model heat flow gradients associated with the sample at a first depth from a sample surface and a second depth from the sample surface, respectively, wherein the first time interval and the second time interval are associated with gradients in heat flow velocity at corresponding depths below a surface of the sample;
control the at least one excitation source to excite the sample at least twice independently from each other with the heat pulses,
control the camera to capture thermal images of the sample surface associated with thermal flows responsive to the heat pulses from the excitation source, so that thermal images are captured at the first time interval and the second time interval with respect to excitation of the sample with the heat pulses, and
evaluate the thermal images to determine a presence of a gradient in heat flow velocity at one or both of the first depth and the second depth.

12. The system according to claim 11, further comprising a memory coupled to the controller and configured to store model heat flow gradients associated with the sample, wherein the controller is configured to select the first time interval and the second time interval based on the stored model heat flow gradients.

13. The system according to claim 11, wherein the controller is further configured to control the camera to capture a plurality of thermal image sequences at the first time interval and the second time interval.

14. The system of claim 11, further comprising a display that displays characteristic curves of intensity versus heat flow after an excitation.

15. The method of claim 1, further comprising displaying characteristic curves of intensity versus heat flow after applying at least one of the first heat pulse and the second heat pulse.

* * * * *

UNITED STATES PATENT AND TRADEMARK OFFICE
CERTIFICATE OF CORRECTION

Page 1 of 1

PATENT NO. : 9,905,014 B2
APPLICATION NO. : 14/653226
DATED : February 27, 2018
INVENTOR(S) : Heissenstein et al.

It is certified that error appears in the above-identified patent and that said Letters Patent is hereby corrected as shown below:

In the Claims

Column 9, Lines 55-57, Claim 1, "to; and indicate a presence" should read --to indicate a presence--

Signed and Sealed this
Tenth Day of March, 2020

Andrei Iancu
*Director of the United States Patent and Trademark Office*